(12) United States Patent
Wolfe et al.

(10) Patent No.: US 12,427,071 B2
(45) Date of Patent: Sep. 30, 2025

(54) IMAGE-BASED PAIRING AND CONTROLLING OF DEVICES IN A CLINICAL ENVIRONMENT

(71) Applicant: Hill-Rom Services, Inc., Batesville, IN (US)

(72) Inventors: Gene J. Wolfe, Pittsford, NY (US); Susan A. Kayser, Batesville, IN (US); Olivia Gubitose Boyce, Cincinnati, OH (US); David L. Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 345 days.

(21) Appl. No.: 17/895,477

(22) Filed: Aug. 25, 2022

(65) Prior Publication Data

US 2023/0062332 A1   Mar. 2, 2023

Related U.S. Application Data

(60) Provisional application No. 63/237,499, filed on Aug. 26, 2021.

(51) Int. Cl.
*A61G 7/018* (2006.01)
*A61B 90/96* (2016.01)
(Continued)

(52) U.S. Cl.
CPC .............. *A61G 7/018* (2013.01); *A61B 90/96* (2016.02); *A61G 7/0506* (2013.01); *F24F 11/50* (2018.01); *G06T 7/13* (2017.01); *G06V 10/46* (2022.01); *G06V 20/44* (2022.01); *G08C 17/02* (2013.01); *H05B 47/115* (2020.01); *A61G 2203/30* (2013.01); *A61G 2203/70* (2013.01);
(Continued)

(58) Field of Classification Search
CPC ......... A61G 7/018; A61B 90/96; F24F 11/50; G06T 7/13; G06V 10/46
See application file for complete search history.

(56) References Cited

U.S. PATENT DOCUMENTS 8,727,981 B2   5/2014   Bechtel et al.
8,743,200 B2   6/2014   Anderson
(Continued)

FOREIGN PATENT DOCUMENTS

CN   215350121   * 4/2021
CN   215385349   * 6/2021
(Continued)

OTHER PUBLICATIONS

Garrido-Jurado, et al., "Automatic Generation and Detection of Highly Reliable Fiducial Markers under Occlusion," Pattern Recognition, vol. 47, Issue 6, Jun. 2014, pp. 2280-2292.

*Primary Examiner* — Quan Zhen Wang
(74) *Attorney, Agent, or Firm* — Lee & Hayes, P.C.

(57) ABSTRACT

An example method includes capturing images using a camera and detecting a medical device in a first image among the images. A request is transmitted to the medical device. Based on transmitting the request, the example method includes determining that the medical device has output a chirp signal in a second image among the images. Based on the chirp signal, the method includes causing the medical device to perform an action by transmitting a control message to the medical device.

20 Claims, 7 Drawing Sheets

(51) Int. Cl.

| | | |
|---|---|---|
| *A61G 7/05* | (2006.01) | |
| *F24F 11/50* | (2018.01) | |
| *F24F 120/14* | (2018.01) | |
| *G06T 7/13* | (2017.01) | |
| *G06V 10/46* | (2022.01) | |
| *G06V 20/40* | (2022.01) | |
| *G08C 17/02* | (2006.01) | |
| *H04B 1/69* | (2011.01) | |
| *H05B 47/115* | (2020.01) | |

(52) U.S. Cl.
CPC ...... *A61G 2205/10* (2013.01); *A61G 2210/70* (2013.01); *A61G 2210/90* (2013.01); *F24F 2120/14* (2018.01); *H04B 2001/6912* (2013.01)

(56) References Cited

U.S. PATENT DOCUMENTS

| | | |
|---|---|---|
| 9,655,546 B2 | 5/2017 | Shen et al. |
| 10,121,070 B2 | 11/2018 | Derenne et al. |
| 10,361,000 B2 | 7/2019 | Johnson et al. |
| 10,372,873 B2 | 8/2019 | Johnson |
| 10,754,924 B2 | 8/2020 | Katz et al. |
| 10,874,794 B2 | 12/2020 | Bechtel et al. |
| 11,065,068 B2 | 7/2021 | Barnett et al. |
| 2005/0200486 A1 | 9/2005 | Greer |
| 2008/0184272 A1 | 7/2008 | Brownewell |
| 2009/0119843 A1* | 5/2009 | Rodgers ............... G16Z 99/00 705/3 |
| 2010/0080431 A1* | 4/2010 | Datema ............... A61B 5/6887 5/601 |
| 2013/0150686 A1 | 6/2013 | Fronterhouse et al. |
| 2015/0294086 A1 | 10/2015 | Kare et al. |
| 2016/0375219 A1* | 12/2016 | Kaikenger ............ A61M 21/00 600/301 |
| 2017/0231545 A1* | 8/2017 | Shinar .................... A61B 5/11 702/150 |
| 2018/0214091 A1* | 8/2018 | Baker ................... A61G 7/018 |
| 2018/0272540 A1 | 9/2018 | Cronin et al. |
| 2019/0231625 A1 | 8/2019 | Nishikado et al. |
| 2020/0312448 A1 | 10/2020 | von Allmen |
| 2020/0350063 A1 | 11/2020 | Thornton et al. |
| 2021/0193310 A1 | 6/2021 | Jacobs et al. |
| 2021/0219873 A1 | 7/2021 | Receveur et al. |
| 2021/0304881 A1* | 9/2021 | White ................... G06K 7/1413 |
| 2022/0125400 A1* | 4/2022 | Wu ......................... G06N 3/02 |

FOREIGN PATENT DOCUMENTS

| | | |
|---|---|---|
| DE | 102016124508 A1 | 6/2018 |
| KR | 102219836 B1 | 2/2021 |

* cited by examiner

IMAGE-BASED PAIRING AND CONTROLLING OF DEVICES IN A CLINICAL ENVIRONMENT

CROSS-REFERENCE TO RELATED APPLICATION

This application claims the priority of U.S. Provisional App. No. 63/237,499, which was filed on Aug. 26, 2021 and is incorporated by reference herein in its entirety.

TECHNICAL FIELD

This application relates generally to techniques for connecting to and controlling remote devices.

BACKGROUND

Hospitals and other clinical environments increasingly rely on a large number of devices to monitor and treat patients. For example, a single patient in a patient room may utilize a smart hospital bed as well as a separate vital sign monitor. These devices may detect various parameters of the patient that are relevant to the patient's condition. However, it may be up to individual care providers to manually review the devices and chart these parameters in the health record. As a result, parameters can be missed and unrecorded. In some cases, a device may automatically chart parameters of the patient. However, when the device is reused for multiple patients, the device may erroneously chart the parameters of a wrong patient if the correct patient is not manually specified by a care provider.

Furthermore, the device can automatically analyze detected parameters in order to recognize that the patient is experiencing a health-related event. For example, a hospital bed may be equipped to determine whether the patient is at risk of developing a pressure injury by determining that the patient has been immobile for some time. In various cases, the device may output an alert that causes a care provider to provide assistance to the patient. However, these techniques also rely on the manual intervention of the care provider. As care providers manage an increasing number of patients, and are exposed to an increasing amount of information, it becomes difficult for care providers to individually take advantage of the increasing amount of patient-related information produced by various devices in clinical environments.

SUMMARY

Various implementations of the present disclosure relate to techniques for pairing devices based on image analysis. Some implementations of the present disclosure relate to remotely controlling devices based on image analysis.

In some example cases, a system is configured to identify a device (e.g., a medical device) in a particular setting, such as a patient room, based on images or video of the particular setting. The system may associate the device with the setting or an individual assigned to the setting (e.g., a patient associated with the room). In some implementations, the system further connects directly to the device.

The system may exert control over the device. For instance, the system may provide alarm thresholds or other evaluation criteria to the device that are specific to the setting or the individual assigned to the setting. In some cases, the system may receive data obtained by the device and analyze and/or store the data based on the existing association between the data and the setting or the individual assigned to the setting.

According to some cases, the system may control a device in the setting based on detecting an event. For example, the system may detect that an individual in the setting is waking up and may therefore cause a lighting system to illuminate the setting. In some cases, the system may cause the device to refrain from performing an action in response to detecting an event. For instance, the system may silence an exit alarm of a hospital bed in response to determining that a care provider is assisting a patient out of the hospital bed. These events may be detected by analyzing images of the setting or other means described herein.

Various implementations of the present disclosure provide improvements to the technical field of automated monitoring, particularly in a healthcare setting. By automatically associating devices with particular settings or individuals, care providers are not required to manually manage or input such associations during their busy workdays. Furthermore, by automatically controlling devices based on detected events in the setting, various systems herein can prevent false alarms and otherwise assist care providers with caring for individuals in the setting.

DESCRIPTION OF THE FIGURES

The following figures, which form a part of this disclosure, are illustrative of described technology and are not meant to limit the scope of the claims in any manner.

DETAILED DESCRIPTION

Figure 1:
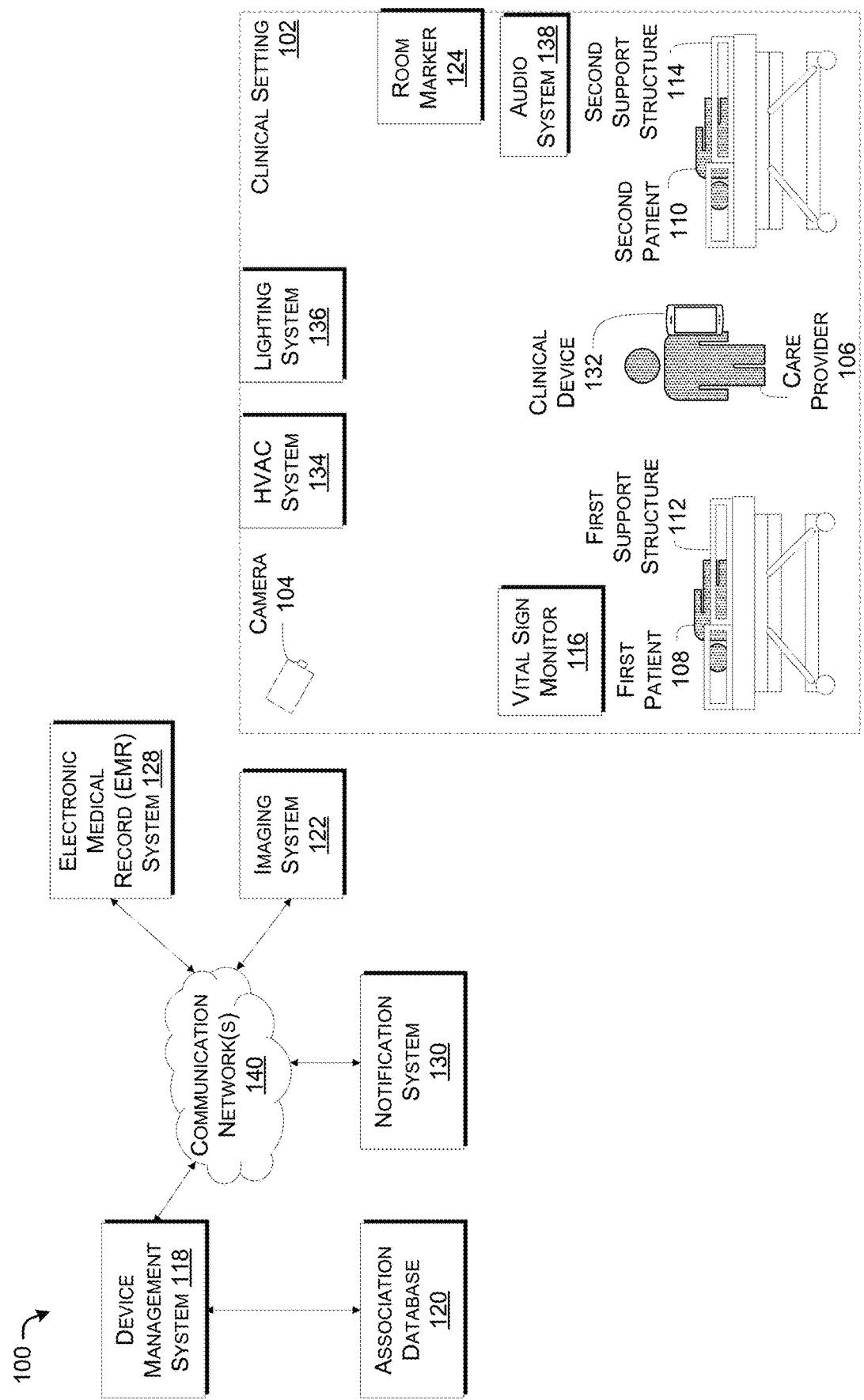
FIG. 1 illustrates an example environment for pairing and controlling of devices within a clinical setting.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 for pairing and controlling of devices within a clinical setting 102. The clinical setting 102 may include at least a portion of one or more rooms within a clinical environment, such as a hospital, a hospice, a medical clinic, or the like. In various examples, the clinical setting 102 is an operating room, an intensive care unit (ICU), a medical ward, a patient ward, or any combination thereof.

The clinical setting 102 may be monitored by a camera 104. The cameras 116 may be configured to capture images and/or video of the clinical setting 102. For example, the camera 104 may include a radar sensor, an infrared (IR) camera, a visible light camera, a depth-sensing camera, or any combination thereof. In various cases, the camera 104 includes one or more photosensors configured to detect light. For example, the photosensor(s) detect visible and/or IR light. In various implementations, the camera 104 includes further circuitry (e.g., an analog-to-digital converter (ADC), a processor, etc.) configured to generate digital data representative of the detected light. This digital data is an image, in various cases. As used herein, the term "image," and its equivalents, refers to a visual representation that includes multiple pixels or voxels. A "pixel" is a datum representative of a discrete area. A "voxel" is a datum representative of a discrete volume. A two-dimensional (2D) image includes pixels defined in a first direction (e.g., a height) and a second direction (e.g., a width), for example. A three-dimensional (3D) image includes voxels defined in a first direction (e.g., a height), a second direction (e.g., a width), and a third direction (e.g., a depth), for example. In various implementations, the camera 104 is configured to capture a video including multiple images of the clinical setting 102, wherein the images can also be referred to as "frames." Although a single camera 104 are depicted in FIG. 1, implementations are not so limited. In some alternate implementations, the clinical setting 102 may include multiple cameras 104.

The clinical setting 102 includes multiple individuals. For example, the clinical setting 102 includes a care provider 106. The care provider 106 may be responsible for caring for patients within the clinical setting 102. The care provider 106 may be, for example, a nurse, a nursing assistant, a physician, a physician's assistant, a physical therapist, medical student, or some other authorized healthcare provider. In various implementations, the clinical setting 104 includes a first patient 108 and a second patient 110.

The first patient 108 is associated with a first support structure 112 and the second patient 110 is associated with a second support structure 114. The first support structure 112 will now be specifically described, and the second support structure 114 may include any of the features of the first support structure 112. The first support structure 112, for example, may be a hospital bed, a gurney, a chair, or any other structure configure to at least partially support a weight of the first patient 108. As used herein, the terms "bed," "hospital bed," and their equivalents, can refer to a padded surface configured to support a patient for an extended period of time (e.g., hours, days, weeks, or some other time period). The first patient 108 may be laying down on the first support structure 112. For example, the first patient 108 may be resting on the first support structure 112 for at least one hour, at least one day, at least one week, or some other time period. In various examples, the first patient 108 and the first support structure 112 may be located in the room. In some implementations, the first support structure 112 includes a mechanical component that can change the angle at which the first patient 108 is disposed. In some cases, the first support structure 112 includes padding to distribute the weight of the first patient 108 on the first support structure 112. According to various implementations, the first support structure 112 can include vital sign monitors configured to output alarms or otherwise communicate vital signs of the first patient 108 to external observers (e.g., care providers, visitors, and the like). The first support structure 112 may include railings that prevent the first patient 108 from sliding off of a resting surface of the first support structure 112. The railings may be adjustable, in some cases.

In various examples, the first support structure 112 includes one or more sensors. For instance, the first support structure 112 may include one or more load cells. The load cell(s) may be configured to detect a pressure on the first support structure 112. In various cases, the load cell(s) can include one or more strain gauges, one or more piezoelectric load cells, a capacitive load cell, an optical load cell, any device configured to output a signal indicative of an amount of pressure applied to the device, or a combination thereof. For example, the load cell(s) may detect a pressure (e.g., weight) of the first patient 108 on the first support structure 112. In some cases, the first support structure 112 includes multiple load cells that respectively detect different pressures on the first support structure 112 in different positions along the first support structure 112. In some instances, the first support structure 112 includes four load cells arranged at four corners of a resting surface of the first support structure 112, which respectively measure the pressure of the first patient 108 on the first support structure 112 at the four corners of the first support structure 112. The resting surface, for instance, can be a surface in which the first patient 108 contacts the first support structure 112, such as a top surface of the first support structure 112.

The first support structure 112 may include one or moisture sensors. The moisture sensor(s) may be configured to measure a moisture on a surface (e.g., the resting surface) of the first support structure 112. For example, the moisture sensor(s) can include one or more capacitance sensors, one or more resistance sensors, one or more thermal conduction sensors, or a combination thereof. In some cases, the moisture sensor(s) include one or more fiber sheets configured to propagate moisture to the moisture sensor(s). In some cases, the moisture sensor(s) can detect the presence or absence of moisture (e.g., sweat or other bodily fluids) disposed between the first support structure 112 and the first patient 108. For example, the moisture sensor(s) may detect a relative difference in inlet vs. outlet moisture of the first support structure 112.

In various examples, the first support structure 112 can include one or more temperature sensors. The temperature sensor(s) may be configured to detect a temperature of at least one of the first patient 108, the first support structure 112, or the room. In some cases, the temperature sensor(s) includes one or more thermistors, one or more thermocouples, one or more resistance thermometers, one or more Peltier sensors, or a combination thereof. In particular examples, the temperature sensor(s) detect a relative difference in inlet vs. outlet temperature of the first support structure 112.

The first support structure 112 may include one or more cameras. For instance, the camera 104 may be part of the first support structure 112. The camera(s) may be configured to capture images of the first patient 108, the first support structure 112, the room, or a combination thereof. In various cases, the camera(s) may include radar sensors, infrared cameras, visible light cameras, depth-sensing cameras, or any combination thereof. In some examples, infrared images may indicate, for instance, a temperature profile of the first patient 108 and/or the first support structure 112. Thus, the camera(s) may be a type of temperature sensor. In addition, the images may indicate a position of the first patient 108 and/or the first support structure 112, even in low-visible-light conditions. For example, the infrared images may capture a position of the first patient 108 during a night environment without ambient lighting in the vicinity of the first patient 108 and/or the first support structure 112. In some cases, the camera(s) may include one or more infrared video cameras. The camera(s) may include at least one depth-sensing camera configured to generate a volumetric image of the first patient 108, the first support structure 112, and the ambient environment. According to various implementations, the images and/or videos captured by the camera(s) are indicative of a position and/or a movement of the first patient 108 over time.

According to some examples, the first support structure 112 can include one or more video cameras (including, e.g., the camera 104). The video camera(s) may be configured to capture videos of the first patient 108, the first support structure 112, the room, an entrance to the room, an entrance to a bathroom adjacent to the room, or a combination thereof. The videos may include multiple images of the first patient 108 and/or the first support structure 112. Thus, the videos captured by the video camera(s) may be indicative of a position and/or movement of the first patient 108 over time. In some examples, the video camera(s) capture visible light videos, changes in radar signals over time, infrared videos, or any combination thereof.

In some examples, the first support structure 112 can include one or more microphones configured to capture audio signals output by the first patient 108, the first support structure 112, and/or the ambient environment. The audio signals captured by the microphone(s) may be indicative of a position and/or movement of the first patient 108 over time. In particular cases, the microphone(s) are integrated within the camera(s) and/or video camera(s).

In some examples, the first support structure 112 includes a head rail and a foot rail. The camera(s) and/or video camera(s), for instance, are mounted on the head rail, the foot rail, an extension (e.g., a metal or polymer structure) attached to the head rail or the foot rail, or any combination thereof. In various implementations, the camera(s) and/or video camera(s) are attached to a wall or ceiling of the room containing the first support structure 112. In some examples, the camera(s) and/or video camera(s) are attached to a cart or other object that is located in the vicinity of the first support structure 112. In some implementations, the camera(s) and/or video camera(s) are integrated with the electronic whiteboard 102.

In various cases, the sensors (e.g., the load cell(s), the moisture sensor(s), the temperature sensor(s), the camera(s), the video camera(s), the microphone, or any combination thereof) of the first support structure 112 are configured to monitor one or more parameters of the first patient 108 and to generate sensor data associated with the first patient 108. In various cases, the sensors convert analog signals (e.g., pressure, moisture, temperature, light, electric signals, sound waves, or any combination thereof) into digital data that is indicative of one or more parameters of the first patient 108. As used herein, the terms "parameter," "patient parameter," and their equivalents, can refer to a condition of an individual and/or the surrounding environment. In this disclosure, a parameter of the first patient 108 can refer to a position of the first patient 108, a movement of the first patient 108 over time (e.g., mobilization of the first patient 108 on and off of the first support structure 112), a pressure between the first patient 108 and an external object (e.g., the first support structure 112), a moisture level between the first patient 108 and the first support structure 112, a temperature of the first patient 108, a vital sign of the first patient 108, a nutrition level of the first patient 108, a medication administered and/or prescribed to the first patient 108, a previous condition of the first patient 108 (e.g., the patient was monitored in an ICU, in dialysis, presented in an emergency department waiting room, etc.), circulation of the first patient 108 (e.g., restricted blood flow), a pain level of the first patient 108, the presence of implantable or semi-implantable devices (e.g., ports, tubes, catheters, other devices, etc.) in contact with the first patient 108, a sound emitted by the first patient 108, or any combination thereof. In various examples, the load cell(s), the moisture sensor(s), the temperature sensor(s), the cameras, the video camera(s), the microphone(s), or a combination thereof, generates sensor data indicative of one or more parameters of the first patient 108.

The first support structure 112 and the second support structure 114 are examples of medical devices. The clinical setting 102 may include other medical devices. As used herein, the term "medical device," and its equivalents, can refer to any machine configured to diagnose, monitor, or treat a patient. For instance, the clinical setting 102 further includes a vital sign monitor 116 configured to detect at least one parameter of the first patient 108. Other examples of medical devices that can be disposed in the clinical setting 102 include ventilators, infusion pumps, nebulizers, feeding tubes, walkers, wheelchairs, humidifiers, dialysis machines, catheters, CPAP machines, imaging devices (e.g., ultrasound imaging devices), intravenous (IV) poles, physiological parameter sensors, and so on.

According to various implementations, medical devices within the clinical setting 102 are configured to generate patient-specific data and may transmit the patient-specific data to a device management system 118. For example, the first support structure 112 is configured to generate data indicative of one or more parameters of the first patient 108 and to transmit the data to the device management system 118. The second support structure 114 is configured to generate data indicative of one or more parameters of the second patient 110 and to transmit the data to the device management system 118. The vital sign monitor 116 is configured to generate data indicative of one or more parameters of the first patient 108 and to transmit the data to the device management system 118.

The device management system 118 may perform various actions based on the patient-specific data received from the medical devices within the clinical setting 102. However, to perform these actions, the device management system 118 may rely on associations between the patients and the patient-specific data. For example, the device management system 118 may generate an alert when a blood pressure detected by the vital sign monitor 116 exceeds a threshold. However, the device management system 118 may further rely on association data indicating that the blood pressure is detected from the first patient 108, rather than the second patient 110. Thus, the device management system 118 may generate the alert to indicate that the first patient 108 has high blood pressure, rather than the second patient 110.

The device management system 118 may include or otherwise communicate with an association database 120 storing the association data. The association data may indicate each patient in the clinical setting 102 that is associated with each medical device in the clinical setting 102. For example, the association database 120 stores association data indicating that the patient-specific data from the first support structure 112 and the vital sign monitor 116 corresponds to the first patient 108, as well as association data indicating that the patient-specific data from the second support structure 114 corresponds to the second patient 110.

Various implementations described herein provide techniques for associating various medical devices in the clinical setting 102 to respective patients in the clinical setting 102. In accordance with particular techniques described in this disclosure, the device management system 118 is configured to generate and store the appropriate association data in the association database 120.

In some cases, the camera 104 captures an image of the clinical setting 102 and provides the image to an imaging system 122. The imaging system 122 may be configured to identify the medical devices in the clinical setting 102 based on the image. For example, the imaging system 122 may perform image recognition on the image to identify the first support structure 112, the second support structure 114, and the vital sign monitor 116.

According to various implementations, the imaging system 122 is configured to identify equipment depicted in the images and/or video. As used herein, the term "object," and its equivalents, may refer to a virtual representation of a physical subject within a digital image or video. In some implementations, the imaging system 122 detects an object representing the equipment using edge detection. The imaging system 122, for example, detects one or more discontinuities in brightness within an image. The one or more discontinuities may correspond to one or more edges of the discrete object representing the equipment in the image. To detect the edge(s) of the object, the imaging system 122 may utilize one or more edge detection techniques, such as the Sobel method, the Canny method, the Prewitt method, the Roberts method, or a fuzzy logic method.

According to some examples, the imaging system 122 identifies the detected object. For example, the imaging system 122 identifies that the object represents the first support structure 112, the second support structure 114, or the vital sign monitor 116 by performing image-based object recognition on the detected object. In some examples, the imaging system 122 uses a non-neural approach to identify the detected object, such as the Viola-Jones object detection framework (e.g., based on Haar features), a scale-invariant feature transform (SIFT), or a histogram of oriented gradients (HOG) features. In various implementations, the image analysis system 114 uses a neural-network-based approach to identify the detected object, such as using a region proposal technique (e.g., R convolutional neural network (R-CNN) or fast R-CNN), a single shot multibox detector (SSD), a you only look once (YOLO) technique, a single-shot refinement neural network (RefineDet) technique, a retina-net, or a deformable convolutional network.

In some cases, the imaging system 122 is configured to track the locations of equipment depicted in the images and/or video. In various implementations, the imaging system 122 tracks the object throughout the multiple images captured by the camera 104. The imaging system 122 may associate the object depicted in consecutive images captured by one of the camera 104. In various cases, the object is representative of a 3D subject within the clinical setting, which can be translated within the clinical setting in three dimensions (e.g., an x-dimension, a y-dimension, and a z-dimension). The imaging system 122 may infer that the subject has moved closer to, or farther away, from the camera 104 by determining that the object representing the subject has changed size in consecutive images. In various implementations, the imaging system 122 may infer that the subject has moved in a direction that is parallel to a sensing face of the camera 104 by determining that the object representing the subject has changed position along the width or height dimensions of the images captured by the camera 104.

Further, because the subject is a 3D subject, imaging system 122 may also determine if the subject has changed shape and/or orientation with respect to the camera 104. For example, the imaging system 122 may determine if the equipment been turned in the clinical setting 102. In various implementations, the imaging system 122 utilizes affine transformation and/or homography to track the object throughout multiple images captured by the camera 104.

In some implementations, an example medical device displays or otherwise visually outputs a code that can be detected by the imaging system 112 in the image. Examples of codes include Quick Response (QR) codes and/or ArUco codes. QR codes and ArUco codes are examples of two-dimensional barcodes. ArUco codes are described, for instance, in S. Garrido-Jurado, et al., PATTERN RECOGN. 47, 6 (June 2014), 2280-92, which is incorporated by reference herein in its entirety. In general, ArUco codes are generated in accordance with a predetermined dictionary of shapes. Based on the dictionary and an image of an example ArUco code, the position (e.g., orientation and distance with respect to the camera capturing the image) can be derived. In various implementations, the code output by the medical device encodes a string, a number, or some other identifier of the medical device. The imaging system 112 may determine the identifier based on the code.

According to some cases, the imaging system 112 may further identify a room in which the medical devices are disposed based on the image. For example, the first patient 108 and the second patient 110 may reside in the same patient room in the clinical setting 102. The room may include a room marker 124 that uniquely identifies the room in the clinical setting 102. For instance, the clinical setting 102 may include multiple rooms, and the room marker 124 may output a code that is uniquely associated with the room containing the first patient 108 and the second patient 110 and is not associated with any other room in the clinical setting 102. Alternatively, the camera 104 may be permanently mounted in the room containing the first patient 108 and the second patient 110.

The imaging system 122 may indicate the recognized medical devices to the device management system 118. In some cases, the imaging system 122 may further identify the room containing the medical devices and/or the camera 104 that has captured the image of the room. Based on the information from the imaging system 122, the device management system 118 may determine that the first support structure 112, the second support structure 114, and the vital sign monitor 116 are located in the room of the clinical setting 102. In some cases, the device management system 118 stores, in the association database 120, association data indicating that the identified medical devices are located in the particular patient room.

In some implementations, the device management system 118 further identifies which medical devices are associated with which patients in the patient room. In some implementations, the imaging system 122 is configured to identify the first patient 108 and the second patient 110 in the image captured by the camera 104. In some cases, the imaging system 122 may identify the first patient 108 and the second patient 110 using facial recognition. The imaging system 122 may identify one or more facial features of the first patient 108 and the second patient 110. As used herein, the term "facial feature," and its equivalents, may refer to a visual characteristic of an individual's face. For example, the imaging system 122 may determine a ratio between specific landmarks of the face of the first patient 108 or the second patient 110, such a ratio of distances between the mouth, nose, eye, jawline, ears, forehead, cheeks, or other facial landmarks. In some cases, the imaging system 122 may determine variances between the face of the first patient 108 or the second patient 110 and a set of eigenfaces in order to recognize the first patient 108 or the second patient 110. Other facial recognition techniques are possible, such as elastic bunch graph matching (e.g., using Fisherfaces), hidden Markov models, dynamic link matching, linear discriminant analysis, multilinear subspace learning, or any combination thereof.

In some examples, the imaging system 122 further determines that the first support structure 112 and the vital sign monitor 116 are actively monitoring the first patient 108, and also that the second support structure 114 is actively monitoring the second patient 110. For instance, the imaging system 122 determines, based on the image, that the first patient 108 is in contact with, resting on, or is otherwise hooked up to the first support structure 112 and the vital sign monitor 116. Similarly, the imaging system 122 may determine, based on the image, that the second patient 110 is in contact with, resting on, or is otherwise coupled to the second support structure 114. The imaging system 122 may provide, to the device management system 118, an indication of which medical devices are monitoring the individual patients in the clinical setting 102.

According to some examples, the device management system 118 determines which medical devices are associated with which patients in the patient room by interfacing with an electronic medical record (EMR) system 128. The EMR system 128 may store EMR data about various patients, including the first patient 108 and the second patient 110. In some instances, the EMR system 128 stores an indication of the patient room in which the first patient 108 and the second patient 110 are located. The EMR system 128 be communicatively coupled to the device management system 118. The EMR system 128, in some cases, transmits data indicating that the first patient 108 and the second patient 110 are located in (e.g., assigned to) the patient room of the clinical setting 102. Accordingly, the device management system 118 may identify the first patient 108 and the second patient 110 in the clinical setting 102 based on identifying the patient room corresponding to the first patient 108 and the second patient 110 depicted in the image.

The device management system 118 is configured to generate the association data and store the association data in the association database 120. By interfacing with the imaging system 122, the device management system 118 can generate the association data without relying on manual inputs from users, such as the care provider 106. In implementations in which the device management system 118 is unable to conclude that a medical device is associated with the first patient 108 or the second patient 110, the device management system 118 may indicate the ambiguity in the association database 120. Thus, the device management system 118 may be prevented from relying on speculative or erroneous association data 120.

In various instances, the device management system 118 can perform various actions based on the association data in the association database 120. In some cases, the medical devices in the clinical setting 102 may transmit the patient-specific data to the device management system 118. The device management system 118 may perform one or more actions based on the association data stored in the association database 120 and the parameters indicated in the patient-specific data.

According to some examples, the imaging system 122 may receive additional images from the camera 104. The imaging system 122 may identify an event depicted in the additional images and indicate the event to the device management system 118. As used herein, the term "event," and its equivalents, may refer to detected features that match a predetermined pattern of features. Examples of specific events include railings on the first support structure 110 being lowered, sheets on the first patient 108 being moved and/or removed, legs of the first patient 108 rotating, the first patient 108 waking up, the first patient 108 sitting up, the legs of the first patient 108 being hooked around an edge of the first support structure 110, the first patient 108 moving toward an edge of the first support structure 110, the first patient 108 standing up, or a combination thereof. Other examples of events include detection of a code blue signal, the first patient 108 experiencing a seizure, the first patient 108 experiencing a fall, one or more parameters of the first event 108 being consistent with sepsis, and so on. Subjects corresponding to objects that can be tracked to identify the event(s) include, for example, the first patient 108, the legs of first patient 108, a sheet on the first support structure 110, the feet of the first patient 108, the hands of the first patient 108, the head of the first patient 108, the face of the first patient 108, or any combination thereof. In some cases, the device management system 118 may perform one or more actions based on the association data stored in the association database 120 and the event detected by the imaging system 122.

For instance, the device management system 118 may update or modify the EMR data stored in the EMR system 128. In some examples, the device management system 118 may generate a message specifying a particular patient and details about the patient and may transmit the message to the EMR system 128. The device management system 118 may identify the particular patient based on the association data in the association database 120. The device management system 118 may generate the details based on the patient-specific data generated by at least one of the medical devices, based on the event detected by the imaging system 122, or a combination thereof. For example, the device management system 118 may generate a message indicating a weight of the second patient 110 detected by the second support structure 114 and may transmit the message to the EMR system 128. The EMR system 128, in turn, may update an EMR of the second patient 110 based on the message from the device management system 118.

In some examples, the device management system 118 and a notification system 130 may generate and output an alert associated with a patient. For example, the device management system 118 may determine that a particular patient is in need of immediate medical attention based on the patient-specific data generated by at least one of the medical devices, based on the event detected by the imaging system 122, or a combination thereof. In some cases, the device management system 118 may generate the alert based on determining that a parameter of the patient (e.g., a respiratory rate) is greater than a first threshold and/or lower than a second threshold. In some examples, the detection of one or more events (e.g., detection of a patient fall) may cause the device management system 118 to conclude that the patient is in need of attention.

The device management system 118 may transmit a message to the notification system 130 that causes the notification system 130 to transmit the alert to one or more external devices, such as a clinical device 132 carried by or otherwise associated with the care provider 106. The clinical device 132 may be a computing device, such as a mobile phone, a laptop, a tablet computer, a smart television (TV), a desktop computer, a smart watch, or any other device including a processor configured to execute operations. The notification system 130 may distribute the alert to various types of devices, such as electronic whiteboards, screens at nurse stations, computing devices, and so on. The external device(s) may output the alert to one or more users. For instance, the clinical device 132 may output, to the care provider 106, an alert indicating that the first patient 108 is in need of assistance. Upon receiving the alert, the care provider 106 may attend to the needs of the first patient 108.

In some examples, the device management system 118 may generate an alert when a first parameter and/or event satisfies particular criteria. Further, the device management system 118 may adjust the particular criteria based on a second parameter and/or event. In particular cases, the device management system 118 is configured to generate an alert if a first parameter of the second patient 110 is above a first threshold or is below a second threshold. However, the device management system 118 may increase or decrease the first threshold and/or the second threshold based on a value of a second parameter or upon detection of an event associated with the second patient 110.

According to various implementations, the device management system 118 may control devices in the clinical setting 102 based on the association data, a parameter, a detected event, or any combination thereof. In some examples, the device management system 118 transmits a message to a support structure (e.g., the first support structure 112 or second support structure 114) that causes the support structure to adjust an angle at which a supported patient (e.g., the first patient 108 or the second patient 110) is disposed, that causes the support structure to raise or lower a railing that could prevent the patient from sliding off the support structure, or the like. In some examples, the device management system 118 transmits a message to the vital sign monitor 116 indicating a threshold or criterion that the vital sign monitor 116 subsequently uses to alarm based on a parameter of the first patient 106.

In various cases, there may be non-medical devices in the clinical setting 102 that can eb controlled by the device management system 118. In some examples, the device management system 118 controls a heating, ventilation, and air conditioning (HVAC) system 134 associated with the identified patient room based on a detected parameter and/or event. For instance, the device management system 118 may cause the HVAC system 134 to lower a temperature of the patient room based on detecting that a temperature of the second patient 110 or the second support structure 114 exceeds a threshold temperature and/or upon detecting an event indicating that the second patient 110 is overheated (e.g., visible sweating by the second patient 110, reddening cheeks of the second patient 110, the second patient 110 removing sheets from the second support structure 114, etc.). In some cases, the device management system 118 may cause the HVAC system 134 to increase a temperature of the patient room upon determining that a temperature of the second patient 110 or the second support structure 114 is below a threshold temperature and/or an event indicating that the second patient 110 is chilled (e.g., shivering by the second patient 110, extending sheets over the face of the second patient 110, etc.).

The device management system 118 may be configured to control a lighting system 136 associated with the identified patient room based on a detected parameter and/or event. The lighting system 136 may include one or more light emitters (e.g., one or more light-emitting diodes (LEDs)) configured to illuminate the identified patient room. The device management system 118 may cause the lighting system 136 to dim the lighting in the identified patient room based on a parameter and/or event indicating that the first patient 108 has fallen asleep. The device management system 118 may cause the lighting system 136 to brighten the lighting in the identified patient room based on a parameter and/or event indicating that the first patient 108 has woken up. In some cases, the device management system 118 may cause the lighting system 136 to brighten the lighting in the identified patient room based on a parameter and/or event indicating that the first patient 108 is in need of immediate assistance from the care provider 106. For example, the device management system 118 may cause the lighting system 136 to brighten the lighting in response to detecting a "code blue" scenario, in which one or more parameters of the first patient 108 indicate that the first patient 108 is in cardiac and/or respiratory arrest. Thus, the care provider 106 may be provided with enough illumination to address the medical emergency of the first patient 108.

In some implementations, the device management system 118 is configured to control an audio system 138 associated with the identified patient room based on a detected parameter and/or event. The audio system 138 may include one or more speakers configured to output sound into the identified patient room. For example, the audio system 138 may include a television or some other device configured to output audible signals into the patient room. The device system 118 may cause the audio system 138 to mute sound based on a parameter and/or event. For example, the device system 118 may cause the audio system 138 to mute the sound based on determining that the second patient 110 has fallen asleep or is in a "code blue" status.

In some examples, the device management system 118 is configured to track the statuses of items in the clinical setting 102 that are imaged by the camera 104. The device management system 118 may store indications of those statuses in the association database 120. For example, the device management system 118 may detect that the vital sign monitor 116 has been sanitized by detecting that the care provider 106 has wiped the vital sign monitor 116 down with antiseptic prior to coupling the vital sign monitor 116 to the first patient 108. The device management system 118 may store, in an entry of the association database 120 corresponding to the vital sign monitor 116, a flag indicating that the vital sign monitor 116 has been sanitized. However, once the device management system 118 detects that the vital sign monitor 116 is coupled to the first patient 108, the device management system 118 may store a flag indicating that the vital sign monitor 116 is unsanitized. If the device management system 118 detects that the unsanitized vital sign monitor 116 is being prepared for use for another patient, such as the second patient 110, the device management system 118 may cause the notification system 130 to output an alert indicating that the vital sign monitor 116 should be sanitized.

In some examples, the imaging system 122 may detect an event involving one of the patients in the clinical setting 102 and the device management system 118 may control a device in the clinical setting 102 based on the event. For example, the imaging system 122 may detect, based on an image and/or video captured by the camera 104, that the first patient 108 is getting out of the first support structure 112 without assistance from the care provider 106. The imaging system 122 may indicate the detected event to the device management system 118. The device management system 118 may also determine, based on the EMR of the first patient 108 stored in the EMR system 128, that the first patient 108 is allowed to exit the support structure 112 without assistance from the care provider 106. Accordingly, the device management system 118 may cause the first support structure 112 to silence a bed exit alarm. In addition, the device management system 118 may control the lighting system 136 to illuminate a walkway from the first support structure 112 to a bathroom in order to prevent the first patient 108 from falling.

Various messages and signals described herein with respect to FIG. 1 can be transmitted over one or more communication networks 140. As used herein, the term "communication network," and its equivalents, may refer to at least one device and/or at least one interface over which data can be transmitted between endpoints. For instance, the communication network(s) 140 may represent one or more communication interfaces traversing the communication network(s). Examples of communication networks include at least one wired interface (e.g., an ethernet interface, an optical cable interface, etc.) and/or at least one wireless interface (e.g., a BLUETOOTH interface, a WI-FI interface, a near-field communication (NFC) interface, a Long Term Evolution (LTE) interface, a New Radio (NR) interface, etc.). In some cases, data or other signals are transmitted between elements of FIG. 1 over a wide area network (WAN), such as the Internet. In some cases, the data include one or more data packets (e.g., Internet Protocol (IP) data packets), datagrams, or a combination thereof.

Various elements described with respect to FIG. 1 can be implemented in hardware and/or software. For example, the various systems and monitors illustrated in FIG. 1 may be implemented in one or more computing devices (e.g., servers) located within or remote from the clinical environment. Various systems and monitors described herein may be implemented by at least one processor configured to execute operations. In some cases, instructions for performing the operations are stored in a (non-transitory) computer readable medium and/or memory.

Figure 2:
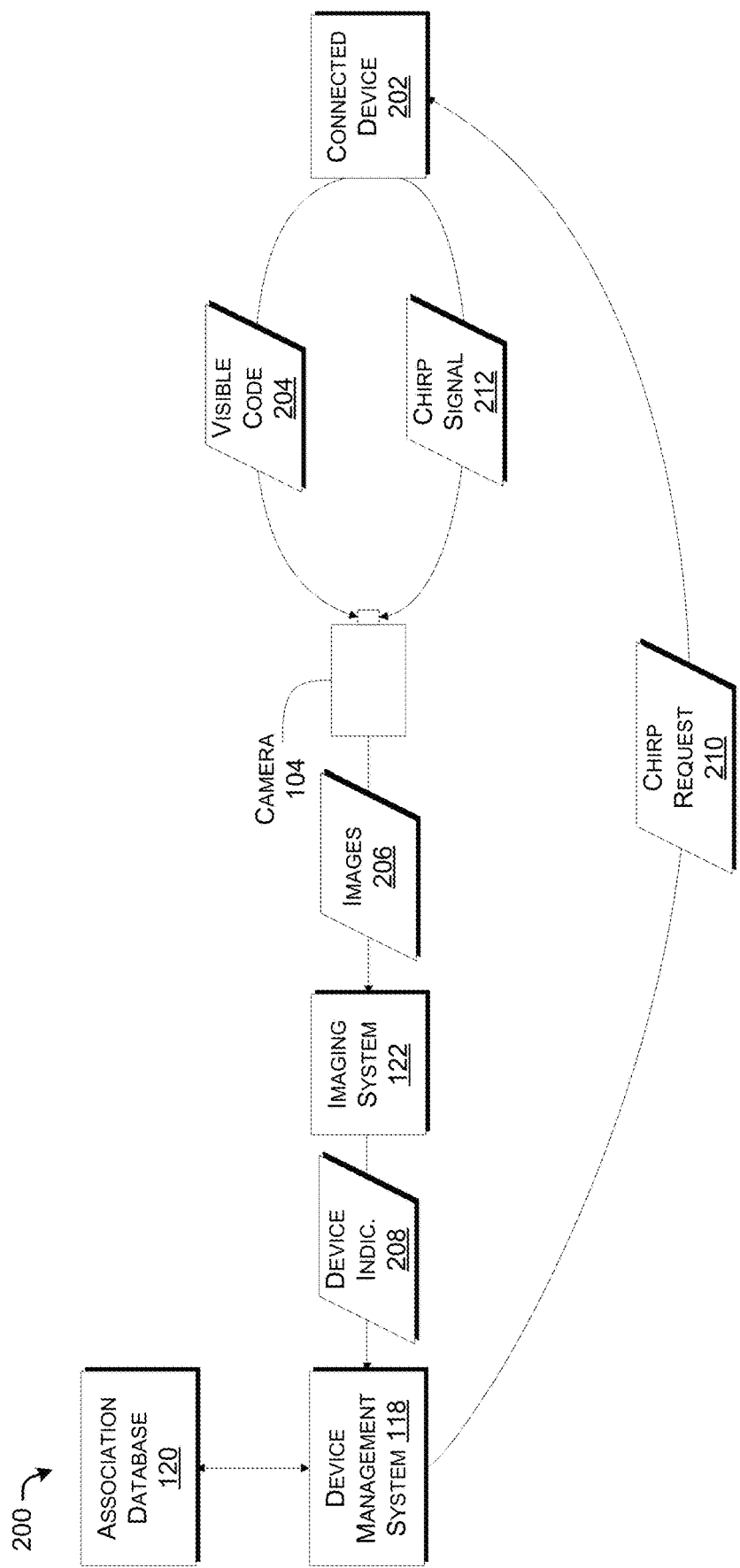
FIG. 2 illustrates example signaling for associating a connected device with a particular location or geographic setting.

FIG. 2 illustrates example signaling 200 for associating a connected device 202 with a particular location or geographic setting. Examples of the connected device 202 include medical devices, such as the first support structure 112, the second support structure 114, or the vital sign monitor 116 described above with reference to FIG. 1. The signaling 200 is also between the camera 104, the device management system 118, the association database 120, and the imaging system 122 described above with reference to FIG. 1. Any signal illustrated in FIG. 2 may be in the form of one or more data packets and/or datagrams transmitted over one or more communication networks, such as the communication network(s) 140 described above with reference to FIG. 1.

In various implementations, the connected device 202 may output a visible code 204. In some examples, the visible code 204 may be painted or printed to the connected device 202. For instance, the visible code 204 may be printed on a sticker that is attached to the connected device 202. According to some cases, the visible code 204 is displayed by the connected device 202. For example, the visible code 204 may be at least temporarily displayed on a screen of the connected device 202. The visible code 204 may encode a string, number, image, or other data that uniquely identifies the connected device 202. In some examples, the visible code 204 includes an address of the connected device 202 that can be used to transmit data to the connected device 202. For instance, the visible code 204 may encode an IP address and/or a MAC address of the connected device 202. In some examples, the visible code 204 is in the form of a barcode, a QR code, an ArUco code, an image, or any combination thereof.

The camera 104 captures images 206 of the connected device 202. For example, the camera 104 may capture images of a space (e.g., a patient room) in which the connected device 202 is disposed. In various examples, at least one of the images 206 depicts the visible code 204 output by the connected device 206. In some implementations, the images 206 further depict an identifier of the space being captured. For example, the images 206 include a visible code displayed in the space that uniquely identifies the space. In some instances, the space is a patient room and the images 206 depict a room number displayed within the patient room. The camera 104 is configured to forward the images 206 to the imaging system 122 for further analysis. In some examples, the images 206 further indicate an identity of the camera 104 that captured the images 206. For example, the images 206 may include metadata indicating an identifier of the camera 104.

The imaging system 122 may be configured to analyze the images 206 captured by the camera 104. In various implementations, the imaging system 122 identifies the visible code 204 depicted in the images 206. The imaging system 122 may identify the connected device 202 based on the visible code 204. For instance, the imaging system 122 may include or access a database including entries that specify codes associated with various devices in the clinical environment. The imaging system 122 may identify the connected device 202 by identifying the entry specifying the visible code 204. In various implementations, the entry may also indicate an identifier of the connected device 202, such as a type of the connected device 202 (e.g., whether the connected device 202 is a vital sign monitor, a support structure, or some other type of device), an address of the connected device 202 (e.g., an IP address), a capability of the connected device 202, or any combination thereof.

In various cases, the imaging system 122 may identify the connected device 202 using a different technique. For example, the imaging system 122 may extract an outline of the connected device 202 using edge detection, determine a color of the connected device 202, or may determine other image-based characteristics of the connected device 202 based on the images 206. In some cases, the imaging system 122 may include or access a database including entries that include various characteristics of devices in the clinical environment. The imaging system 122 may identify the connected device 202 by identifying an entry of the database that is consistent with the identified characteristics of the connected device 202. In various implementations, the entry may also indicate an identifier of the connected device 202, such as a type of the connected device 202 (e.g., whether the connected device 202 is a vital sign monitor, a support structure, or some other type of device), an address of the connected device 202 (e.g., an IP address), a capability of the connected device 202, or any combination thereof.

In addition, the imaging system 122 may identify the space in which the connected device 202 is disposed. For example, the imaging system 122 may identify the visible code output within the patient room in which the connected device 202 is located. In some examples, the imaging system 122 may utilize image recognition techniques to identify the space depicted in the images 106. In some cases, the imaging system 122 identifies one or more features in the space based on the images 106. The feature(s) may be unique to the space, such that the space can be identified based on the feature(s).

The imaging system 122 may provide a device indicator 208 to the device management system 118. The device indicator 208 includes the identifier of the connected device 202 that is encoded by the visible code 204. According to some implementations, the device indicator 208 further includes the identifier of the space (e.g., the patient room) in which the connected device 202 is disposed. In some cases, the device indicator 208 indicates the identifier of the camera 104 that captured the images 206.

The device management system 118 may determine the location of the connected device 202 based on the device indicator 208. For example, the device management system 118 may identify the connected device 202 based on the identifier of the connected device 202 included in the device indicator 208. In various examples, the device management system 118 may further identify the space in which the connected device 202 is disposed. For example, the device management system 118 identifies the space based on the identifier of the space and/or the identifier of the camera 104 included in the device indicator 208. In cases wherein the camera 104 is permanently installed in a single space, the identifier of the camera 104 may also uniquely identifies the space in which the camera 104 is disposed. By identifying the connected device 202 and the space, the device management system 118 may determine the location of the connected device 202.

In various cases, the device management system 118 may store an indication of the connected device 202 and the space in the association database 120. In some examples, the device management system 118 may further identify a patient associated with the space. For instance, the device management system 118 may pull EMR data from an EMR system that indicates the patient is assigned or otherwise resides in the space depicted in the images 206. The device management system 118, in some cases, may further indicate an identity of the patient in the association database 120. For example, an entry of the association database 120 may include an identity of the connected device 202, an identity of the space, an identity of the camera 104, an identity of the patient assigned to the space, or any combination thereof. Accordingly, the device management system 118 may be able to associate the connected device 202 with a particular space and/or patient in a clinical environment.

In some implementations, the device management system 118 may further confirm the location of the connected device 202. The device management system 118 may identify an address of the connected device 202. For example, the identifier included in the device indication 208 may include the address of the connected device 202. In some examples, the device management system 118 may retrieve the address from a look-up table that correlates the identifier of the connected device 202 and the address of the connected device 202.

The device management system 118 may generate a chirp request 210 addressed to the connected device 202. For example, the chirp request 210 includes a field that includes the address of the connected device 202. In some implementations, the chirp request 210 causes the connected device 202 to output a chirp signal 212. The chirp signal 212 is discernable to the camera 104, in some cases. For example, the chirp signal 212 is a visible signal, such as a shape displayed on a screen of the connected device 202, a flashing light, a movement of the connected device 202, etc. In some examples, the camera 104 includes a microphone and the chirp signal 212 is an audible signal output by a speaker of the connected device 202. In various implementations, the chirp signal 212 is included in at least one of the images 206 provided to the imaging system 122. The imaging system 122 may detect the chirp signal 212 in the images 206 and may indicate, in the device indication 208, that the connected device 202 output the chirp signal 212. Thus, the device management system 118 may confirm that the connected device 202 output the chirp signal 212. In various implementations, the chirp signal 212 can be used to confirm that the connected device 202 has been properly identified and located by the device management system 118.

In various implementations, the chirp request 210 includes provisioning information for the connected device 202. In some cases, the chirp request 210 includes information that enables the connected device 202 to transmit data to the device management system 118 over one or more communication networks. The chirp request 210 may include an address (e.g., an IP address and/or a MAC address) of the device management system 118. For instance, based on the chirp request 210, the connected device 202 may transmit one or more parameters of a patient to the device management system 118. In some implementations, the chirp request 210 includes an identifier (e.g., a numeric code) that corresponds to the room in which the connected device 202 is disposed and/or the patient being monitored by the connected device 202. The connected device 202 may include the identifier of the room and/or patient in the data it transmits to the device management system 118. Accordingly, if the device management system 118 is connected to multiple connected devices, the device management system 118 may be able to efficiently identify the patient corresponding to the data received from the connected device 202.

In some implementations, the provisioning information in the chirp request 210 enables the connected device 202 to monitor the patient. For example, the chirp request 210 may include one or more alarm criteria corresponding to an emergency condition of the patient. In some cases, the chirp request 210 includes one or more patient-specific thresholds. For instance, when the device management system 118 is aware of the patient being monitored by the connected device 202, the device management system 118 may relay the patient-specific threshold(s) from an EMR of the patient to the connected device 202. In various implementations, the connected device 202 may detect a parameter of the patient and may alarm when the parameter fulfills the one or more alarm criteria. For example, the connected device 202 may output a visual signal (e.g., a blinking light), may output an audible signal (e.g., a siren), or may vibrate when a detected parameter exceeds a first threshold or is less than a second threshold, wherein the first and second thresholds are indicated in the chirp request. In some cases, the connected device 202 may transmit, to the device management system 118, a message indicating an alarm if the parameter fulfills the one or more alarm criteria. In some cases, the connected device 202 may output the chirp signal 212 in response to provisioning itself with the provisioning information in the chirp request 210. For instance, the connected device 202 may output the chirp signal 212 when the connected device begins to apply the one or more emergency criteria.

Figure 3:
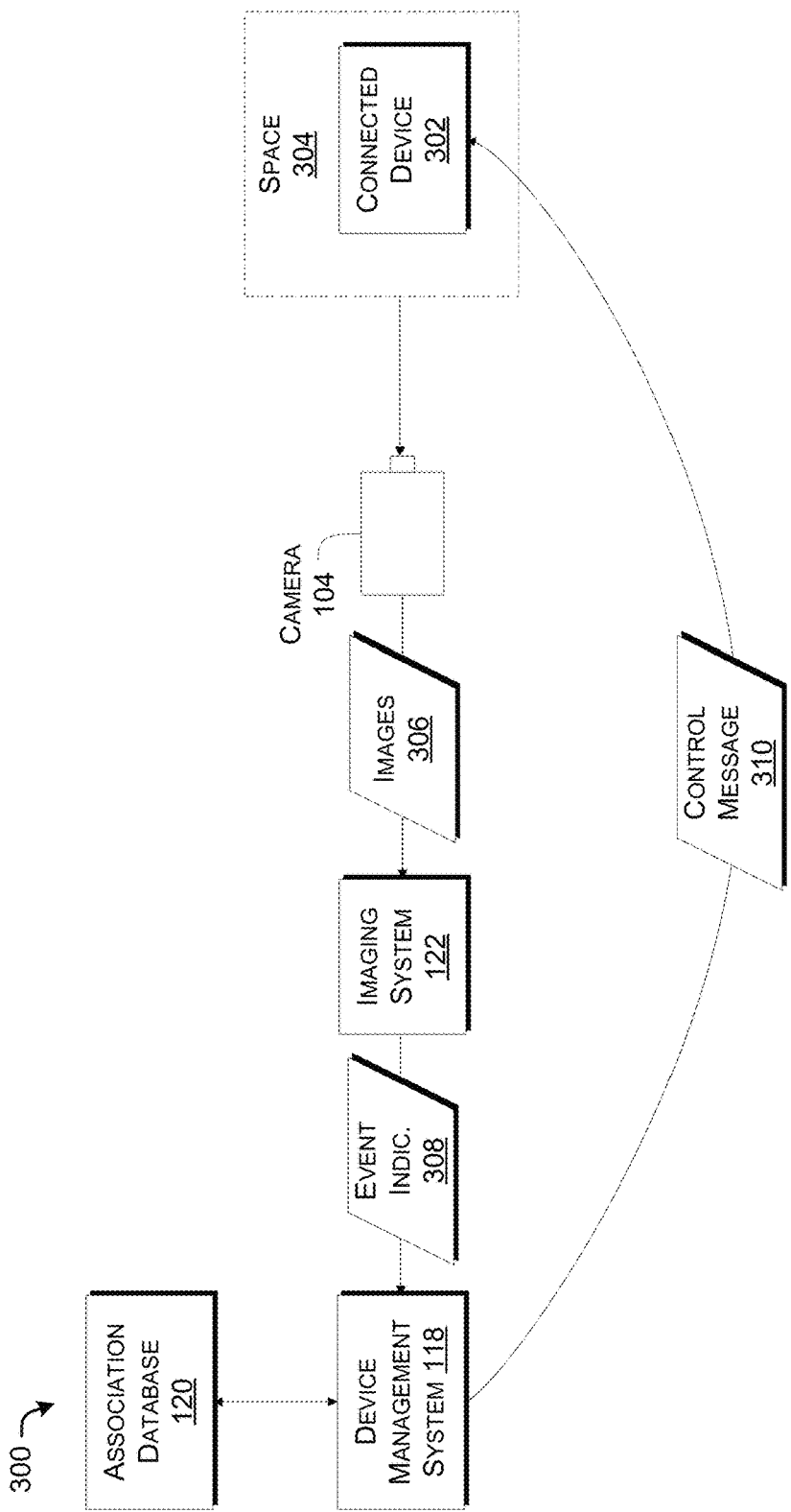
FIG. 3 illustrates example signaling for controlling a connected device based on image-based detection of events.

FIG. 3 illustrates example signaling 300 for controlling a connected device 302 based on image-based detection of events. Examples of the connected device 302 include the connected device 202 and/or medical devices, such as the first support structure 112, the second support structure 114, or the vital sign monitor 116 described above with reference to FIG. 1. The signaling 300 is also between the camera 104, the device management system 118, the association database 120, and the imaging system 122 described above with reference to FIG. 1. Any signal illustrated in FIG. 3 may be in the form of one or more data packets and/or datagrams transmitted over one or more communication networks, such as the communication network(s) 140 described above with reference to FIG. 1.

The connected device 302 is disposed inside of a space 304. In alternate implementations, the connected device 302 is disposed outside of the space 304. The space 304, for example, is in a clinical setting. In some implementations, the space 304 is a patient room. For example, the space 304 may include a patient, a care provider, a visitor, a medical device, a television, a window, or any combination thereof. Various subjects within the space 304 may move around and/or change appearance over time.

The camera 104 captures images 306 of the space 304. In some cases, the camera 104 is also disposed in the space 304. The images 306, in various examples, include a video of the space 304. For example, the images 306 may indicate movement of any of the subjects within the space 304, locations and orientations of any subjects within the space 304, and changes in appearance and/or states of the subjects within the space 304. The camera 104 provides the images 306 to the imaging system 122.

The imaging system 122 may be configured to identify an event depicted in the images 306. Examples of events include railings of a support structure being lowered, sheets on a patient being moved and/or removed, legs of the patient rotating, the patient waking up, the patient sitting up, the legs of the patient being hooked around an edge of the support structure, the patient moving toward an edge of the support structure, the patient standing up, a code blue signal being activated, the patient experiencing a seizure, the patient experiencing a fall, one or more parameters of the patient being consistent with sepsis, or any combination thereof.

The imaging system 122 may identify the event by identifying and/or tracking objects in the images 306. The imaging system 122 may detect objects indicative of subjects, such as the patient, the legs of the patient, a sheet of the patient, the feet of the patient, the hands of the patient, the head of the patient, the face of the patient, or any combination thereof. Any of the various image processing techniques described herein can be used to identify and/or track the objects.

In various implementations, the imaging system 122 outputs an event indication 308 to the device management system 118. In various cases, the device management system 118 stores one or more rules and/or algorithms that cause the device management system 118 to perform one or more actions based on the event. These actions may include internal actions. For example, the device management system 118 may adjust a sensitivity of another analysis based on the event indicated in the event indication 308. For instance, the device management system 118 may raise or lower a threshold based on the event indication 308, and may trigger an alarm if a patient parameter is greater than the adjusted threshold.

In some implementations, the device management system 118 controls the connected device 302 based on the detected event. In various implementations, the device management system 118 may identify the connected device 302 based on an entry in the association database 120. For example, the association database 120 may indicate that the connected device 302 is located in the space 304 in which the event occurred and/or the space 304 monitored by the camera 104. In some cases, the entry includes an address (e.g., an IP address and/or MAC address) of the connected device 302. The device management system 118 may generate a control message 310 addressed to the connected device 302. The device management system 118 may transmit the control message 310 to the connected device 302. In various implementations, the control message 310 may include an instruction to perform an action. For example, the connected device 302 may adjust an alarm threshold that the connected device 302 compares to a physiological parameter, the connected device 302 may adjust a bed angle of a support structure supporting a patient in the space 304, the connected device 302 may adjust the temperature of the space 304, the connected device 302 may adjust lighting in the space 304, or the connected device 302 may adjust a volume of an audio signal output into the space 304.

Figure 4:
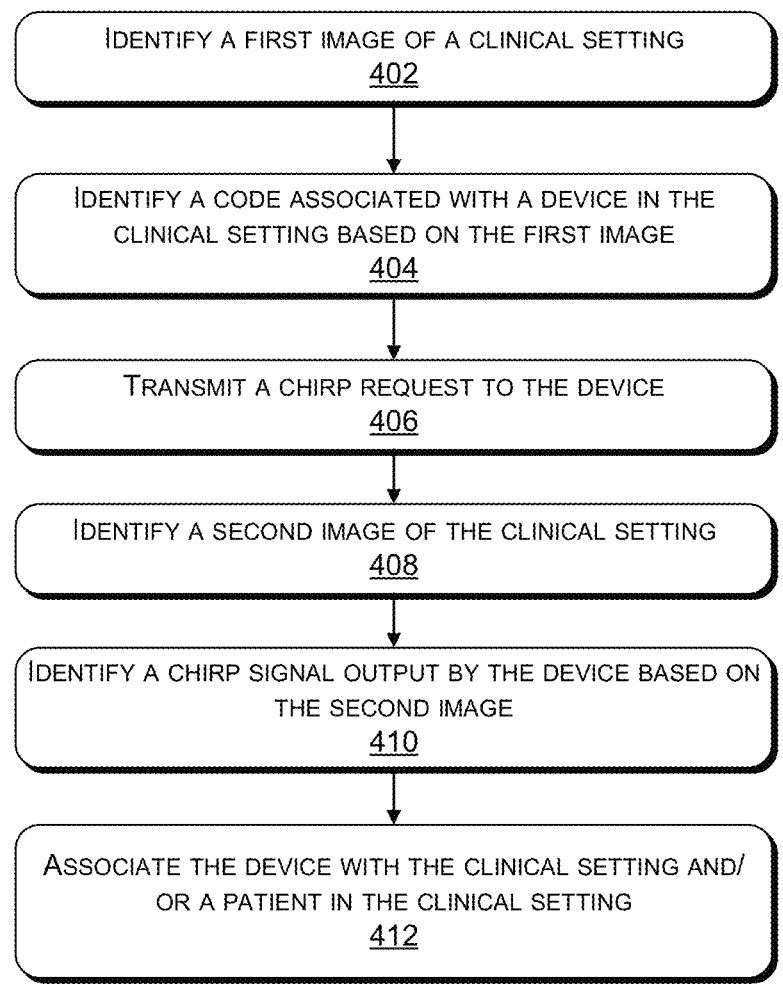
FIG. 4 illustrates an example process for associating a device with a person or environment.

FIG. 4 illustrates an example process 400 for associating a device with a person or environment. The example process 400 may be performed by an entity that includes, for example, the device management system 118, the imaging system 122, the association database 120, a processor, a computing device, or any combination thereof.

At 402, the entity identifies a first image of a clinical setting. The image, for example, is captured by a camera. In some cases, the clinical setting includes an individual (e.g., a care provider, a patient, etc.) and a device. The device, for example, may be a medical device, such as a support structure (e.g., a hospital bed) or a vital sign monitor. Furthermore, in some implementations, the clinical setting may include a room or other predetermined space. In various implementations, the entity identifies the individual, the device, the room, or any combination thereof, using various image processing techniques described herein.

At 404, the entity identifies a code associated with the device in the clinical setting based on the first image. The code may indicate an identifier of the device. In some implementations, the code is printed on the device itself and/or a substrate affixed to the device. For instance, the code maybe displayed on a sticker that is attached to the device. In some cases, the code is displayed on a display screen of the device. The code, for example, is a barcode (e.g., a QR code or an ArUco code). In some implementations, the code is indicative of an identifier of the device, such as an address (e.g., an IP address or MAC address) of the device.

At 406, the entity transmits a chirp request to the device. The entity may identify the address of the device based on the code. In some cases, the entity retrieves the address of the device by accessing an entry of a database storing the identifier of the device. In some implementations, the code itself indicates the address of the device. The entity may transmit the chirp request a data packet with the address of the connected device as the destination address of the data packet. In some examples, the chirp request is a pairing request between the entity and the device. In various implementations, the device outputs a chirp signal based on the chirp request. For example, the device outputs the chirp signal upon establishing a connection with the entity. In various implementations, the chirp signal may be visually output by the device. For example, the chirp signal may be visually displayed on a screen of the device or may be a signal output by a light on the device (e.g., a predetermined blinking light pattern).

At 408, the entity identifies a second image of the clinical setting. The second image may depict the chirp signal output by the device. In some cases, the entity identifies multiple second images (e.g., a video) indicating the chirp signal. At 410, the entity identifies a chirp signal output by the connected device based on the second image.

At 412, the entity associates the device with the clinical setting and/or a patient in the clinical setting. According to various implementations, the entity may determine the clinical setting by analyzing the first image and/or the second image. For example, the entity may identify a room number or room name displayed within the clinical setting depicted in the first image and/or the second image. In various implementations, the entity may determine the patient associated with the clinical setting. For example, the entity may access a database storing the identity of the patient in the same entry as an identifier (e.g., number or room) of the room. In some implementations, the entity associates the device with the clinical setting and/or the patient by transmitting an indication of the clinical setting and/or the patient to the device itself. In some implementations, the entity may transmit a threshold or other analysis criterion associated with the patient in order to enable the device to monitor the patient based on the threshold or other analysis criterion directly. In some cases, the entity transmits a message instructing the device to store a parameter of the patient in an EMR of the patient. According to some implementations, the entity associates the device with the clinical setting and/or the patient by storing an indication of the device with the identifier of the room or patient in an entry of a database. When the entity receives a message from the device, the entity may use the entry of the database to infer that the message is about the clinical setting and/or the patient. For instance, the device may transmit an indication of a detected parameter of the patient to the entity. By referring to the entry, the entity may identify an EMR of the patient and store the indication of the detected parameter in the EMR.

Figure 5:
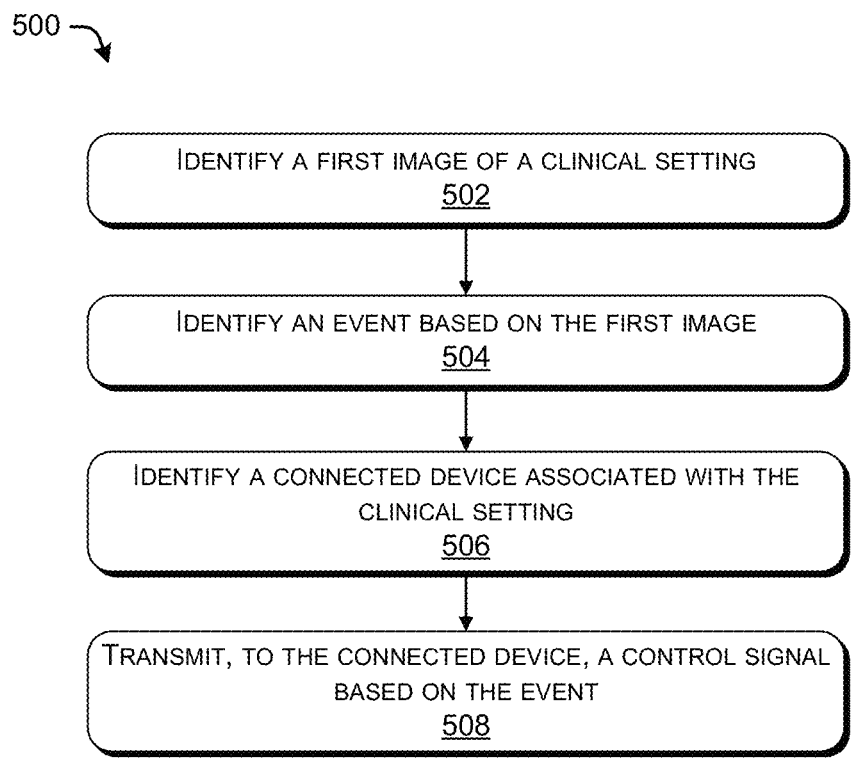
FIG. 5 illustrates an example process for controlling a device.

FIG. 5 illustrates an example process 500 for controlling a device. The example process 500 may be performed by an entity that includes, for example, the device management system 118, the imaging system 122, the association database 120, a processor, a computing device, or any combination thereof.

At 502, the entity identifies a first image of a clinical setting. The image, for example, is captured by a camera. In some cases, the clinical setting includes an individual (e.g., a care provider, a patient, etc.) and a device. The device, for example, may be a medical device, such as a support structure (e.g., a hospital bed) or a vital sign monitor. Furthermore, in some implementations, the clinical setting may include a room or other predetermined space. In various implementations, the entity identifies the individual, the device, the room, or any combination thereof, using various image processing techniques described herein.

At 504, the entity identifies an event based on the first image. In some implementations, the event is based on the patient in the clinical setting. The event, for example, may include railings of a support structure being lowered, sheets on a patient being moved and/or removed, legs of the patient rotating, the patient waking up, the patient sitting up, the legs of the patient being hooked around an edge of the support structure, the patient moving toward an edge of the support structure, the patient standing up, a code blue signal being activated, the patient experiencing a seizure, the patient experiencing a fall, one or more parameters of the patient being consistent with sepsis, or any combination thereof.

At 506, the entity identifies a connected device associated with the clinical setting. In some examples, the connected device is pre-associated with the patient or the clinical setting. For example, the entity may store an entry in a database indicating that the connected device is associated with the patient and/or the clinical setting. In some examples, the connected device is a medical device, such as a support structure supporting the patient or a vital sign monitor monitoring the patient. In some implementations, the connected device includes a speaker, a heater, an air conditioner, a vent, or a light. For instance, the connected device could be a television, an HVAC system, or a lighting system.

At 508, the entity transmits, to the connected device, a control signal based on the event. For example, the control signal may cause the support structure to adjust a pressure in an air bladder, adjust an angle of the support structure, or mute a bed exit alarm. In some examples, the control signal causes the vital sign monitor to output an alarm, adjust a threshold that the vital sign monitor uses to assess a parameter of the patient, or the like. In various implementations, the control signal causes the speaker to mute; the heater, air conditioner, or vent to increase or decrease a temperature of the clinical setting; or the light to increase or decrease illumination in the clinical setting.

Figure 6:
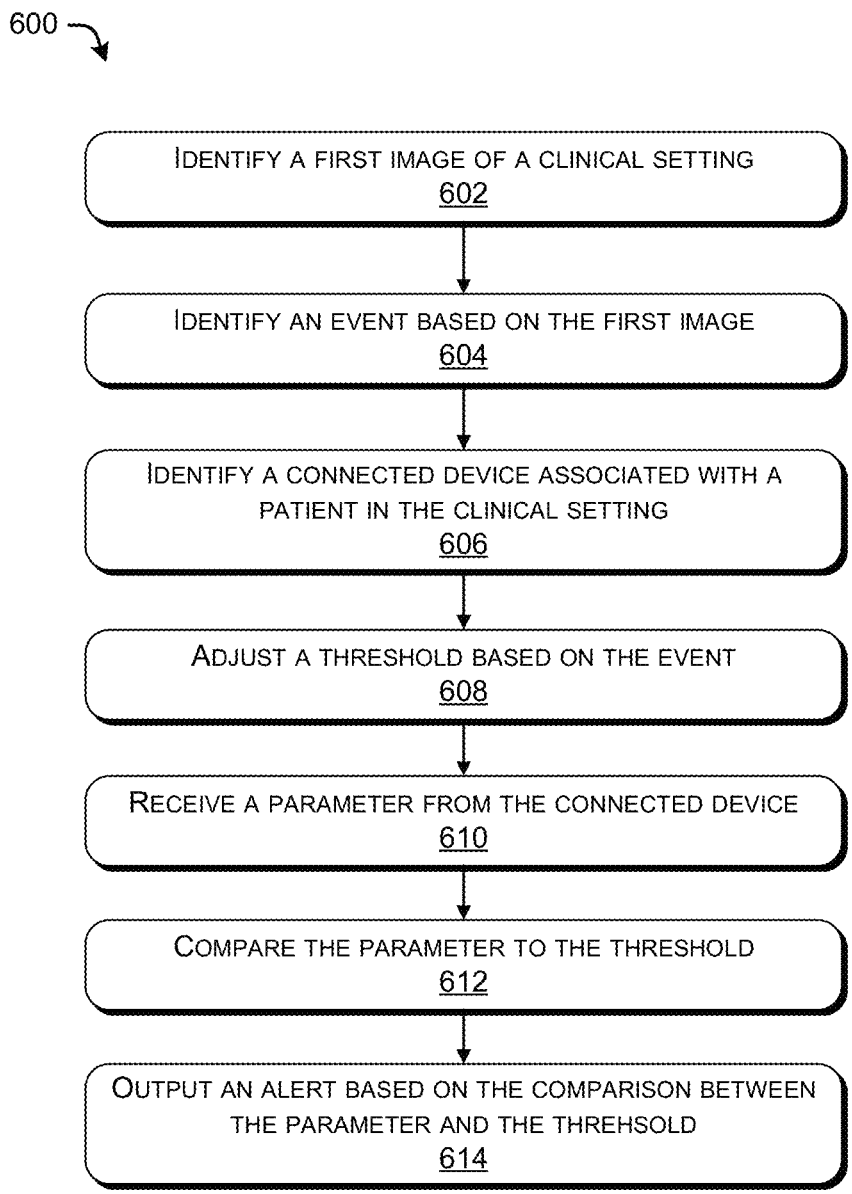
FIG. 6 illustrates an example process for adjusting monitoring thresholds of a connected device based on events.

FIG. 6 illustrates an example process 600 for adjusting monitoring thresholds of a connected device based on events. The example process 600 may be performed by an entity that includes, for example, the device management system 118, the imaging system 122, the association database 120, a processor, a computing device, or any combination thereof.

At 602, the entity identifies a first image of a clinical setting. In some cases, the clinical setting includes an individual (e.g., a care provider, a patient, etc.) and a device. The device, for example, may be a medical device, such as a support structure (e.g., a hospital bed) or a vital sign monitor. Furthermore, in some implementations, the clinical setting may include a room or other predetermined space. In various implementations, the entity identifies the individual, the device, the room, or any combination thereof, using various image processing techniques described herein.

At 604, the entity identifies an event based on the first image. In some implementations, the event is based on the patient in the clinical setting. The event, for example, may include railings of a support structure being lowered, sheets on a patient being moved and/or removed, legs of the patient rotating, the patient waking up, the patient sitting up, the legs of the patient being hooked around an edge of the support structure, the patient moving toward an edge of the support structure, the patient standing up, a code blue signal being activated, the patient experiencing a seizure, the patient experiencing a fall, one or more parameters of the patient being consistent with sepsis, or any combination thereof.

At 606, the entity identifies a connected device associated with a patient in the clinical setting. In some examples, the connected device is pre-associated with the patient or the clinical setting. For example, the entity may store an entry in a database indicating that the connected device is associated with the patient and/or the clinical setting. In some examples, the connected device is a medical device, such as a support structure supporting the patient or a vital sign monitor monitoring the patient.

At 608, the entity adjusts a threshold based on the event. In various implementations, a patient condition may be assessed based on a parameter of the patient being above or below the threshold. The event may indicate that the threshold itself should be adjusted in order to more accurately identify the condition of the patient. For example, sepsis may be associated with fever, a low blood pressure, and a high respiratory rate. The entity may detect, based on a video of the patient in the clinical setting, that the patient is feverish by detecting that the patient is shivering or sweating. Because these events are associated with an increased likelihood that the patient is septic, the entity may increase a blood pressure threshold and/or decrease a respiratory rate threshold for detecting sepsis.

At 610, the entity receives a parameter from the connected device. For example, the connected device may transmit an indication of a vital sign of the patient, such as blood pressure or respiratory rate. At 612, the entity compares the parameter to the threshold.

At 614, the entity outputs an alert based on the comparison between the parameter and the threshold. For example, if the entity determines that the blood pressure of the patient is below the blood pressure threshold and/or that the respiratory rate of the patient is above the respiratory rate threshold, then the entity may output an alert indicating that the patient is suspected of having sepsis. The alert may be output to a clinical device, which may output a signal to a care provider based on the alert. The care provider may provide assistance to the patient.

Figure 7:
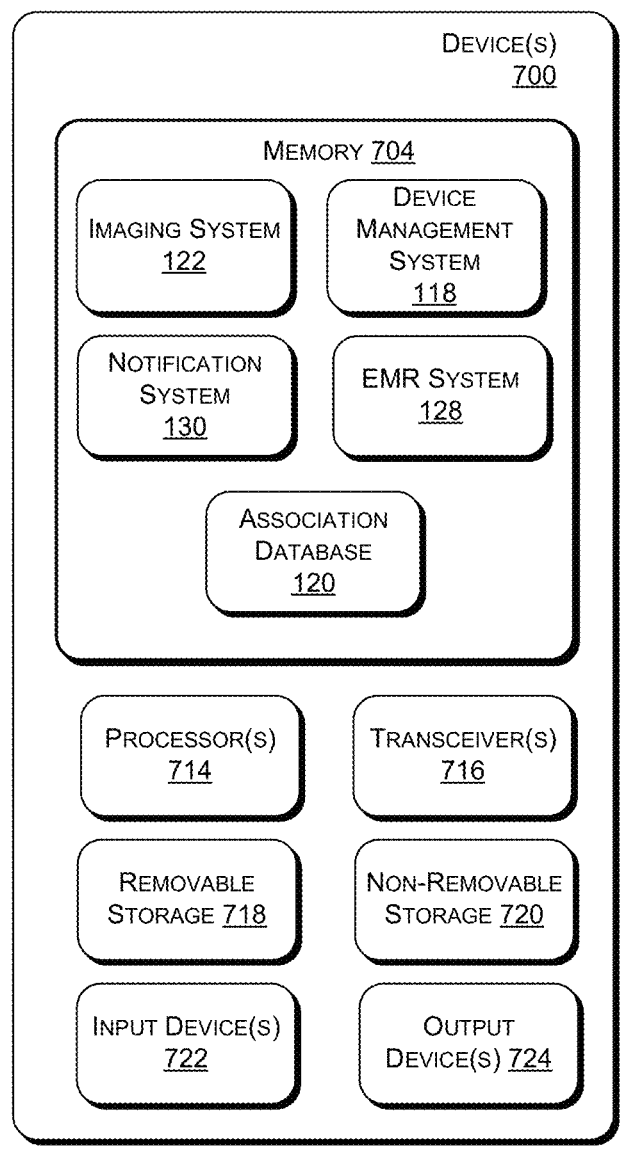
FIG. 7 illustrates at least one example device configured to enable and/or perform the some or all of the functionality discussed herein.

FIG. 7 illustrates at least one example device 700 configured to enable and/or perform the some or all of the functionality discussed herein. Further, the device(s) 700 can be implemented as one or more server computers 702, a network element on a dedicated hardware, as a software instance running on a dedicated hardware, or as a virtualized function instantiated on an appropriate platform, such as a cloud infrastructure, and the like. It is to be understood in the context of this disclosure that the device(s) 700 can be implemented as a single device or as a plurality of devices with components and data distributed among them.

As illustrated, the device(s) 700 comprise a memory 704. In various embodiments, the memory 704 is volatile (including a component such as Random Access Memory (RAM)), non-volatile (including a component such as Read Only Memory (ROM), flash memory, etc.) or some combination of the two.

The memory 704 may include various components, such as the device management system 118, the association database 120, the imaging system 122, the EMR system 128, and the notification system 130. Any of the device management system 118, the association database 120, the imaging system 122, the EMR system 128, and the notification system 130 can comprise methods, threads, processes, applications, or any other sort of executable instructions. The device management system 118, the association database 120, the imaging system 122, the EMR system 128, and the notification system 130 and various other elements stored in the memory 704 can also include files and databases.

The memory 704 may include various instructions (e.g., instructions in the device management system 118, the association database 120, the imaging system 122, the EMR system 128, and the notification system 130), which can be executed by at least one processor 714 to perform operations. In some embodiments, the processor(s) 714 includes a Central Processing Unit (CPU), a Graphics Processing Unit (GPU), or both CPU and GPU, or other processing unit or component known in the art.

The device(s) 700 can also include additional data storage devices (removable and/or non-removable) such as, for example, magnetic disks, optical disks, or tape. Such additional storage is illustrated in FIG. 7 by removable storage 718 and non-removable storage 720. Tangible computer-readable media can include volatile and nonvolatile, removable and non-removable media implemented in any method or technology for storage of information, such as computer readable instructions, data structures, program modules, or other data. The memory 704, removable storage 718, and non-removable storage 720 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 700. Any such tangible computer-readable media can be part of the device(s) 700.

The device(s) 700 also can include input device(s) 722, such as a keypad, a cursor control, a touch-sensitive display, voice input device, etc., and output device(s) 724 such as a display, speakers, printers, etc. These devices are well known in the art and need not be discussed at length here. In particular implementations, a user can provide input to the device(s) 500 via a user interface associated with the input device(s) 722 and/or the output device(s) 724.

As illustrated in FIG. 7, the device(s) 700 can also include one or more wired or wireless transceiver(s) 716. For example, the transceiver(s) 716 can include a Network Interface Card (NIC), a network adapter, a LAN adapter, or a physical, virtual, or logical address to connect to the various base stations or networks contemplated herein, for example, or the various user devices and servers. To increase throughput when exchanging wireless data, the transceiver(s) 716 can utilize Multiple-Input/Multiple-Output (MIMO) technology. The transceiver(s) 716 can include any sort of wireless transceivers capable of engaging in wireless, Radio Frequency (RF) communication. The transceiver(s) 716 can also include other wireless modems, such as a modem for engaging in Wi-Fi, WiMAX, Bluetooth, or infrared communication.

In some implementations, the transceiver(s) 716 can be used to communicate between various functions, components, modules, or the like, that are comprised in the device(s) 700. For instance, the transceivers 716 may facilitate communications between the device management system 118, the association database 120, the imaging system 122, the EMR system 128, and the notification system 130.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

What is claimed is:

1. A system, comprising:
   at least one processor;
   a camera communicatively coupled to the at least one processor and configured to capture images;
   memory communicatively coupled to the at least one processor and storing instructions that, when executed by the at least one processor, cause the system to perform operations comprising:
   detecting a medical device in a first image among the images;
   transmitting a request to the medical device;
   based on transmitting the request, determining that the medical device has output a chirp signal in a second image among the images; and
   based on determining that the medical device has output the chirp signal, causing the medical device to perform an action by transmitting a control message to the medical device.

2. The system of claim 1, wherein the medical device comprises a vital sign monitor or a hospital bed.

3. The system of claim 1, wherein detecting the medical device in the first image comprises:
   detecting, in the first image, a barcode or ArUco code displayed by the medical device; and
   determining an identifier of the medical device based on the barcode or ArUco code.

4. The system of claim 3, wherein
   the memory further stores a database, and
   the operations further comprise:
   identifying, in the database, an entry comprising the identifier;
   determining an IP address of the medical device based on the entry; and
   generating the request comprising the IP address.

5. The system of claim 1, wherein detecting the medical device in the first image comprises:
   identifying a shape of the medical device by performing edge detection on the first image; and
   identifying the device based on the shape of the medical device.

6. The system of claim 1, wherein determining that the medical device has output a chirp signal comprises determining that the medical device has displayed a pattern and/or determining that a light of the medical device has blinked.

7. The system of claim 1, wherein the control message comprises an instruction to determine whether a parameter of a patient is greater than a first threshold or less than a second threshold and to output an alert based on the parameter of the patient being greater than the first threshold or less than the second threshold.

8. The system of claim 1, further comprising:
   a transceiver configured to receive a signal indicating a parameter of a patient,
   wherein:
   the control message comprises an instruction to transmit the signal to the transceiver, and
   the operations further comprise:
   determining that the parameter is greater than a first threshold or is less than a second threshold; and
   based on determining that the parameter is greater than the first threshold or is less than the second threshold, transmitting an alert to an external computing device.

9. A system, comprising:
   at least one processor;
   a camera communicatively coupled to the at least one processor and configured to capture images of a setting comprising a patient;
   memory communicatively coupled to the at least one processor and storing instructions that, when executed by the at least one processor, cause the system to perform operations comprising:
   determining, based on the images, that the patient is in cardiac or respiratory failure;
   generating a control message based on determining that the patient is in cardiac or respiratory failure;
   causing a lighting system to increase illumination of the setting by transmitting the control message to the lighting system; and
   causing a speaker to mute a sound in the setting based on determining that the patient is in cardiac or respiratory failure.

10. The system of claim 9, wherein the operations further comprise:
    determining, based on the images, that the patient has removed sheets, that a face of the patient is flushed, that the patient is sweating, or that the patient is shivering, and
    causing a heating, ventilation, and air conditioning (HVAC) system to increase or decrease a temperature of the setting.

11. The system of claim 9, wherein the operations further comprise:
    determining, based on the images, that greater than a threshold time has elapsed since a last turn by the patient, and
    based on determining that greater than the threshold time has elapsed since the last turn by the patient, causing a hospital bed to adjust a pressure in an air bladder or to adjust an angle of the hospital bed.

12. The system of claim 9, wherein the operations further comprise:
    determining that a height of the patient is greater than a threshold height, and
    based on determining that the height of the patient is greater than the threshold height, causing a hospital bed to extend a foot rail.

13. The system of claim 9, wherein the operations further comprise:
    determining, based on the images, that the patient has experienced apnea or that the patient is in a position associated with aspiration, and
    in response to determining that the patient has experienced apnea or that the patient is in the position associated with aspiration, causing a hospital bed to change a bed angle.

14. A system, comprising:
    at least one processor;
    a camera communicatively coupled to the at least one processor and configured to capture images of a setting comprising a patient;
    memory communicatively coupled to the at least one processor and storing instructions that, when executed by the at least one processor, cause the system to perform operations comprising:
    detecting, based on the images, an event by determining that the patient is in a predetermined position or has a predetermined movement;
    generating a control message based on the event; and
    causing, by transmitting the control message to a vital sign monitor, the vital sign monitor to refrain from detecting a physiological parameter of the patient or to mute an alarm associated with the physiological parameter.

15. The system of claim 14, wherein the operations further comprise:
   detecting, based on the images, that the patient has removed sheets, that a face of the patient is flushed, that the patient is sweating, or that the patient is shivering, and
   causing a heating, ventilation, and air conditioning (HVAC) system to increase or decrease a temperature of the setting.

16. The system of claim 14, wherein the operations further comprise:
   detecting, based on the images, that the patient is waking up, and
   based on detecting that the patient is waking up, causing a lighting system to increase illumination of the setting.

17. The system of claim 14, wherein the operations further comprise:
   determining, based on the images, that greater than a threshold time has elapsed since a last turn by the patient, and
   based on determining that greater than the threshold time has elapsed since the last turn by the patient, causing a hospital bed to adjust a pressure in an air bladder or to adjust an angle of the hospital bed.

18. The system of claim 14, wherein the operations further comprise:
   detecting, based on the images, that a height of the patient is greater than a threshold height, and
   based on detecting that the height of the patient is greater than the threshold height, causing a hospital bed to extend a foot rail.

19. The system of claim 14, wherein the operations further comprise:
   determining, based on the images, that the patient has experienced apnea, and
   based on determining that the patient has experienced apnea, causing a hospital bed to change a bed angle.

20. The system of claim 14, wherein the operations further comprise:
   determining, based on the images, that the patient is in a position associated with aspiration, and
   based on determining that the patient is in the position associated with aspiration, causing a hospital bed to adjust an angle of the hospital bed.

\* \* \* \* \*